(12) United States Patent
Schmid et al.

(10) Patent No.: US 7,467,005 B2
(45) Date of Patent: Dec. 16, 2008

(54) METHOD AND APPARATUS FOR NON-INVASIVELY MEASURING BLOOD FLOW AND FOR ACQUIRING AND PROCESSING AN ECG SIGNAL

(75) Inventors: Johann-Jakob Schmid, Rifferswil (CH); Jacques Felblinger, Ludres (FR); Roger Abächerli, Baar (CH)

(73) Assignee: Schiller AG, Baar (CH)

( * ) Notice: Subject to any disclaimer, the term of this patent is extended or adjusted under 35 U.S.C. 154(b) by 388 days.

(21) Appl. No.: 10/703,524

(22) Filed: Nov. 10, 2003

(65) Prior Publication Data
US 2004/0097818 A1    May 20, 2004

(30) Foreign Application Priority Data
Nov. 11, 2002    (EP)    .................... 02405969

(51) Int. Cl.
*A61B 5/05*    (2006.01)
(52) U.S. Cl. ..................................... 600/419
(58) Field of Classification Search ......... 600/509–527, 600/41, 504, 407, 419, 505, 420; 359/566
See application file for complete search history.

(56) References Cited

U.S. PATENT DOCUMENTS

| | | | |
|---|---|---|---|
| 3,659,591 A * | 5/1972 | Doll et al. | ................. 600/407 |
| 3,809,070 A | 5/1974 | Doll et al. | |
| 4,412,545 A | 11/1983 | Okino et al. | |
| 4,915,111 A * | 4/1990 | Sano et al. | ................. 600/419 |
| 5,436,564 A | 7/1995 | Kreger et al. | |
| 5,464,014 A | 11/1995 | Sugahara | |
| 5,873,837 A * | 2/1999 | Lieber et al. | ................. 600/504 |
| 5,924,986 A * | 7/1999 | Chandler et al. | ............ 600/407 |
| 5,935,077 A | 8/1999 | Ogle | |
| 5,973,837 A * | 10/1999 | Hasegawa et al. | ........... 359/566 |
| 6,045,504 A | 4/2000 | Muzilla et al. | |
| 6,053,873 A * | 4/2000 | Govari et al. | ............... 600/505 |
| 6,132,380 A | 10/2000 | Cohen et al. | |
| 6,148,229 A | 11/2000 | Morris, Sr. et al. | |
| 6,569,160 B1 * | 5/2003 | Goldin et al. | ................. 606/41 |

FOREIGN PATENT DOCUMENTS

| | | |
|---|---|---|
| AT | 399646 | 6/1995 |
| DE | 4429335 | 3/1995 |
| EP | 0913703 | 5/1999 |

* cited by examiner

*Primary Examiner*—George Manuel
(74) *Attorney, Agent, or Firm*—Shoemaker and Mattare

(57) ABSTRACT

The flow of blood in a vessel (G) in a living being (P) which is exposed to a magnetic field (B) is determined by measuring the potential difference ($\Delta V$) between at least two points (P1, P2) next to the vessel (G). The potential difference ($\Delta V$) is produced on the basis of the Hall effect by the moving charge carriers (Q) in the blood in the presence of the magnetic field (B). When recording an ECG, the cardiac output can be determined in this manner under the influence of a magnetic field (B). At the same time, the ECG signal can be corrected in the knowledge of the component (T) of the ECG signal (E) which can be attributed to the Hall effect.

6 Claims, 6 Drawing Sheets

Figure 1:
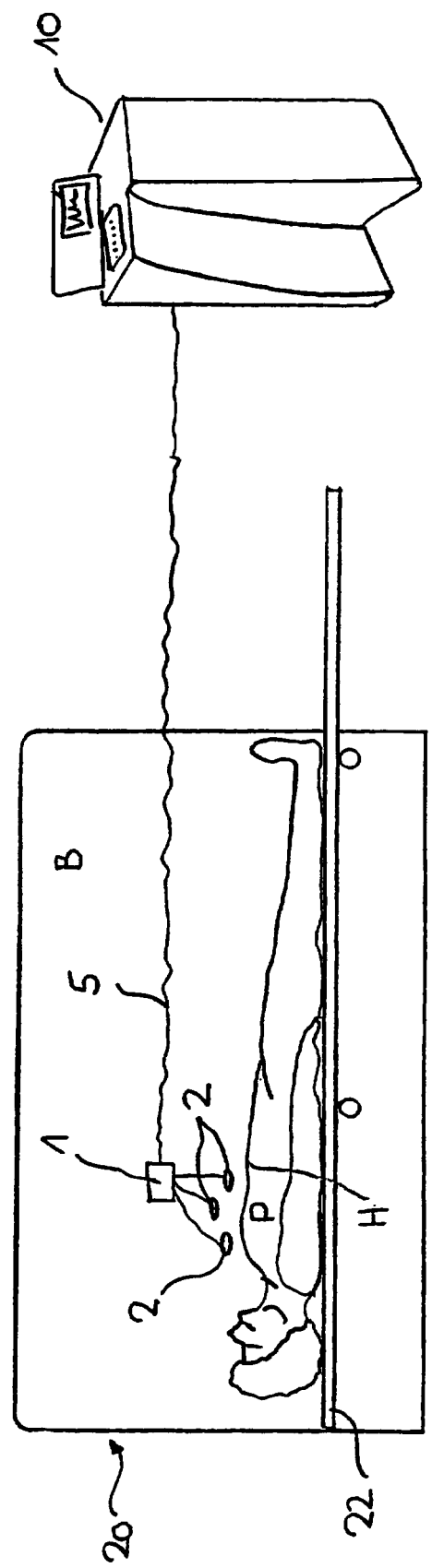

METHOD AND APPARATUS FOR NON-INVASIVELY MEASURING BLOOD FLOW AND FOR ACQUIRING AND PROCESSING AN ECG SIGNAL

The invention relates to a method and an apparatus for non-invasive measurement of the flow of blood and for acquiring and processing an ECG signal, and to the use of an ECG device having the features of the precharacterizing part of the independent patent claims.

The magnitude of the flow of blood in vessels and particularly the blood expelled by the heart (cardiac output) is relevant within the context of a large number of diagnoses. Similarly, the recording of electrocardiograms (ECG) is widely used for diagnostic purposes. Determining the flow of blood and/or recording electrocardiograms can also be helpful while recording MRI images, in particular. Electrocardiograms are used, by way of example, for monitoring patients during MRI. The strong magnetic field which is present and the radio-frequency signals which are used in magnetic resonance imagers mean that ECG signals are frequently subject to interference, however. In particular, the ECG signal becomes overlaid with interference signals. Methods for preventing such interference signals and for transmitting the ECG signal out of the screened interior of an MRI arrangement and also electrodes designed therefore are known, by way of example, from EP 1 050 270, U.S. Pat. Nos. 6,073,030, 6,032,063, 6,052,614, EP 487 441, EP 695 139, U.S. Pat. No. 5,733,247, WO 92/21286, FR 2 685 968, U.S. Pat. No. 4,991,580 or EP 132 785. These different methods relate, in particular, to interference in the electrical signal which is induced on the basis of the strong magnetic field and the radio-frequency signals.

It is an object of the present invention to provide a method with which ECG signals can be acquired precisely even when there are high magnetic fields. Another object of the present invention is to provide a method and an apparatus for non-invasive measurement of the flow of blood.

The invention achieves these objects with a method and with an apparatus having the features of the characterizing part of the independent patent claims. The inventors of the present application have found out that the Hall effect in the region of blood vessels means that potential differences are produced on the basis of movement of the blood when the blood are exposed to a relatively strong magnetic field. A first aspect of the invention is based on the application of this knowledge to the non-invasive measurement of the flow of blood in a blood vessel in a body of a living being. To do this, the body is exposed to a sufficiently strong magnetic field. An electrical potential is derived from at least two points on the body surface. The points are preferably next to the blood vessel in which the flow of blood needs to be determined. The flow of blood is determined on the basis of the potential difference between the at least two points. The determination is based on the knowledge that the potential difference caused by the Hall effect is proportional to the movement of charge carriers in the blood in the vessel and is therefore proportional to the flow of blood. The flow of blood can thus be determined at least quantitatively.

Charge carriers are haemoglobin or ions contained in the blood, for example. The measurement is best when the vessel runs at right angles to the principal magnetic field.

Preferably, the present method involves the magnetic field being produced by an MRI arrangement. MRI arrangements typically produce magnetic fields in the range from 0.5 to 3 tesla. In this case, the inventive method allows the flow of blood to be determined at the same time as an MRI diagnosis is being performed.

The MRI diagnosis allows the cross-section of the blood vessel to be determined at the same time. With knowledge of the cross-section, the flow of blood can also be determined quantitatively.

The potential difference is measured particularly preferably using an inherently conventional ECG device which is designed to record, process and transmit ECG signals even under the influence of strong magnetic fields.

Other devices for measuring electro-physiological parameters are also conceivable, e.g. EEG etc. Reference is made here and below to ECG devices for the purposes of illustration. Other devices can likewise be used.

In line with a further aspect of the present invention, the at least two electrodes of the ECG device are placed on the body of the living being such that the cardiac output of the heart can be determined from the measured potential difference.

In line with a further aspect of the invention, the knowledge is applied to acquiring and processing an ECG signal. The inventors have discovered that, when recording electrocardiograms during MRI, the ECG signal becomes overlaid with a signal part which can be attributed to a potential difference which is produced on the basis of the Hall effect by charge carriers contained in the blood. The invention therefore involves ascertaining a portion of the signal profile which is produced on the basis of the Hall effect by charge carriers in the blood expelled by the heart. The ECG signal is then processed. The part of the ECG signal which is caused by the Hall effect is eliminated. This allows a usable ECG signal to be determined even in a strong magnetic field, such as that present in an MRI arrangement.

In line with one preferred exemplary embodiment, the living being's cardiac output is determined on the basis of the signal profile in the determined portion of the ECG signal, particularly on the basis of the amplitude in this portion.

In line with a further aspect of the invention, an inherently conventional ECG device is used to determine the flow of blood in a vessel in the body of a living being exposed to a magnetic field. In particular, the ECG device is used to determine the cardiac output.

The inventive apparatus is used for non-invasive measurement of the flow of blood in a vessel in a body of a living being. Alternatively, the inventive apparatus can be used to acquire and process an ECG signal. The apparatus is particularly suitable for carrying out one of the methods described above. The apparatus has an ECG arrangement having at least two electrodes for measuring a potential difference between at least two points on the surface of the body of a living being. The ECG arrangement is essentially of conventional design and is suitable for recording ECG signals even under the influence of strong magnetic fields and high-frequency signals.

The inventive apparatus can also have associated means for producing a magnetic field. Typically, these means are formed by a coil in a MRI arrangement. The apparatus is also provided with means for ascertaining a component of the potential signal produced by the ECG arrangement which is produced by the movement of charge carriers in the vessel on the basis of the Hall effect. These means can be implemented particularly preferably using software in a conventional ECG. The inventive apparatus is then a conventional ECG device with additional functions.

Figure 2:
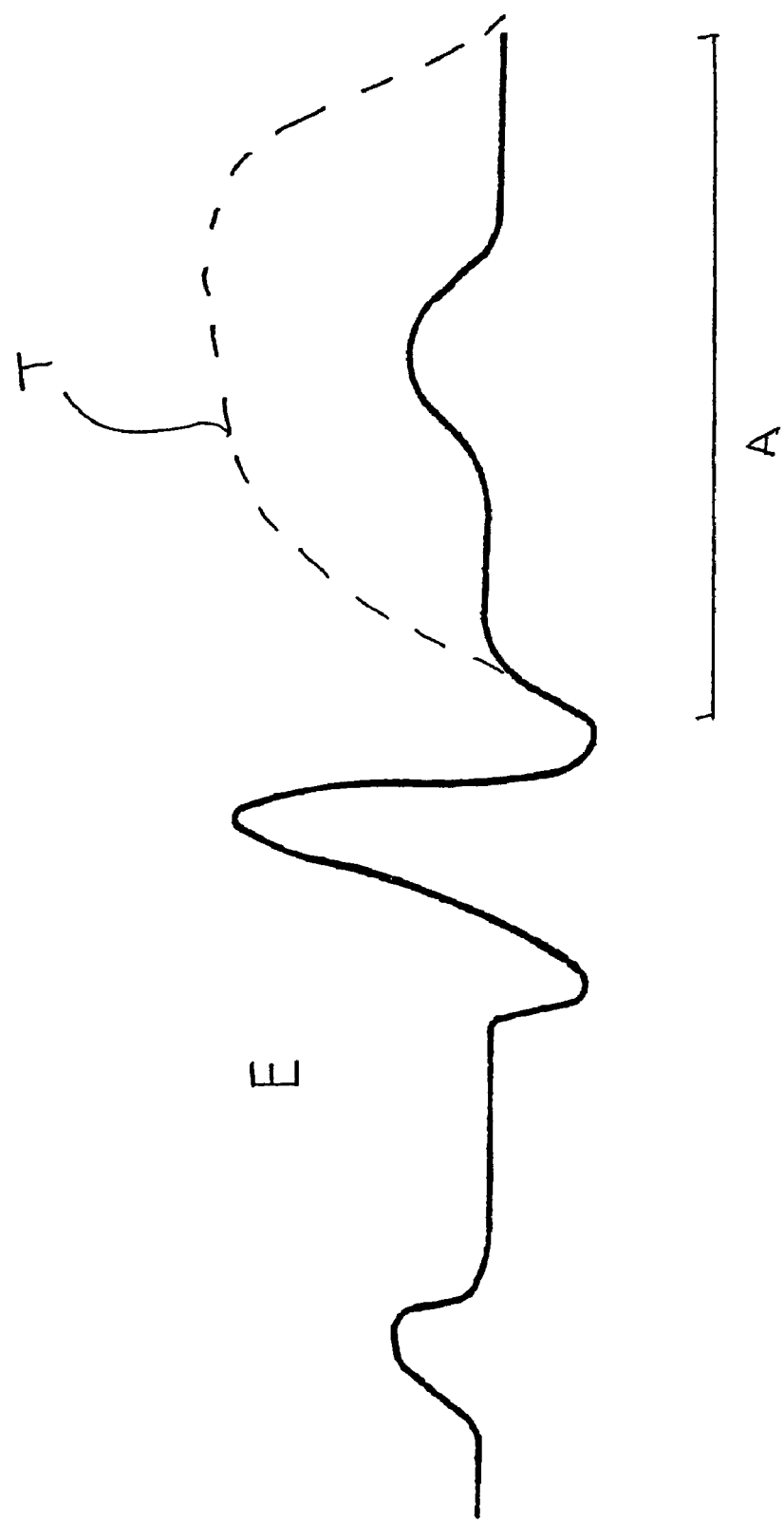
Figure 3:
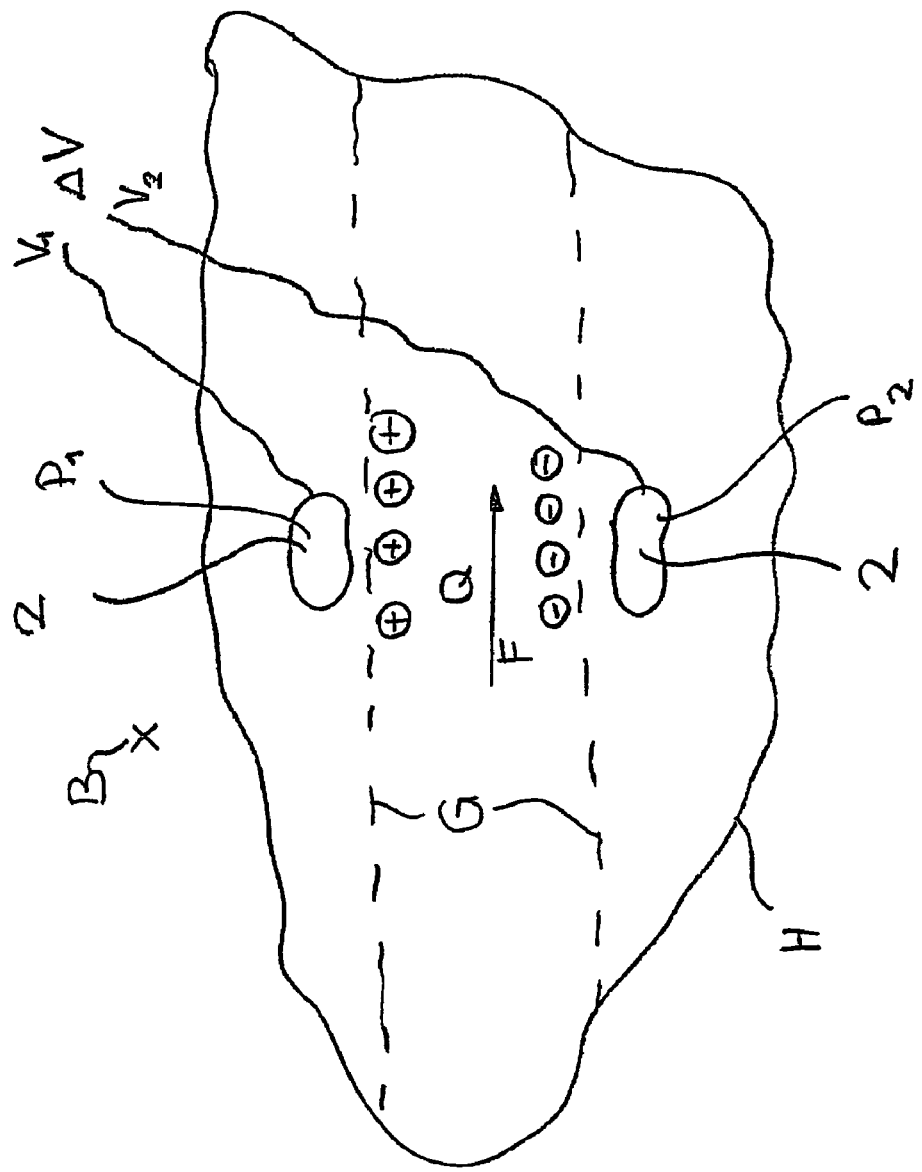
Figure 4:
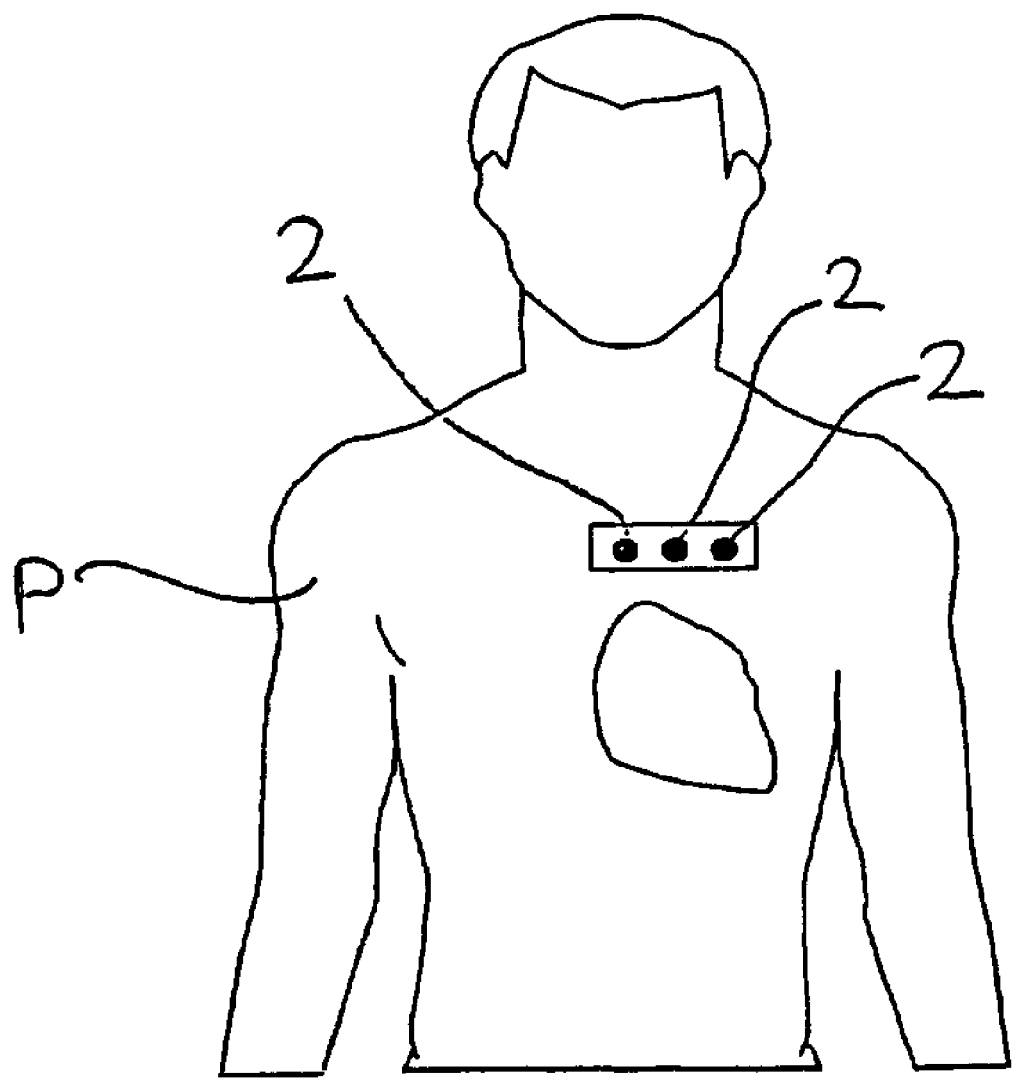
Figure 5A:
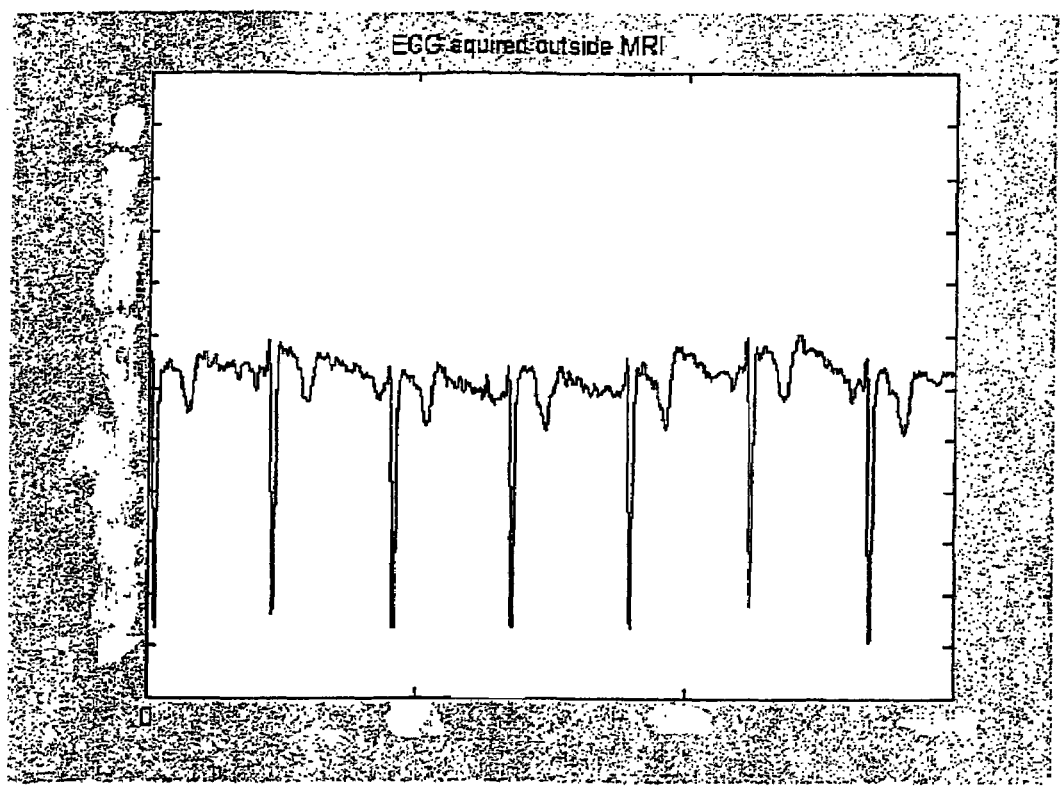

The invention is explained in more detail below in exemplary embodiments and with reference to the drawings, in which:

FIG. 1 shows a schematic illustration of an apparatus in accordance with the invention, FIG. 2 shows a schematic illustration of the profile of an ECG signal, FIG. 3 shows a schematic illustration of the measurement of the flow of blood in a vessel, FIG. 4 shows a schematic illustration of the arrangement of electrodes for determining the cardiac output, and FIGS. 5a and show an illustration of an ECG signal 5b recorded inside and outside a magnetic field.

FIG. 1 schematically shows an inventive apparatus for non-invasive measurement of the flow of blood and for recording and processing an electrocardiogram. The apparatus essentially comprises an ECG arrangement 1 which is connected to an evaluation and display device 10 by means of a cable 5. Transmission by radio or on an optical path are also conceivable. The ECG arrangement 1 is arranged inside an MRI arrangement 20. Inside the MRI arrangement 20, there is a magnetic field B of high strength, typically a 0.5 to 5 tesla. A patient P can be moved on a displaceable bed 22 into the tunnel (not shown in more detail) of the MRI arrangement 20. The MRI arrangement 20 is used for recording an MRI image and is designed in a manner which is known per se. To measure the flow of blood and to record ECGs, the ECG arrangement is provided with electrodes 2 which are positioned on the skin H of the patient P.

FIG. 2 shows the profile of an ECG signal which is recorded using the inventive apparatus. An ordinary ECG signal E is shown in a solid line. The ECG signal E has been attained using the ECG arrangement, for example, when the MRI arrangement 20 is not in operation, i.e. when no strong magnetic field B is present. Using a dashed line, FIG. 2 shows a portion A of the ECG signal which is conditioned by the magnetic field B on the basis of the Hall effect. As soon as an ECG needs to be recorded when the MRI arrangement is operating, the actual ECG signal E is overlaid with a signal part T which can be attributed to the Hall effect. The signal part T interferes with the electrocardiogram. Attempts are therefore made to eliminate this signal part. The apparatus therefore contains means for ascertaining the portion A and for eliminating the component T of the ECG curve E which can be attributed to the Hall effect. These means are typically arranged in the display and evaluation device 10. It is alternatively conceivable for the means to be implemented using software in a conventional ECG arrangement.

The parasitic part of the ECG curve can be determined by template matching, for example, in a manner which is known per se to a person skilled in the art.

The part T of the ECG curve E which is caused by the Hall effect can alternatively be evaluated for further purposes. The blood contains charge carriers. On the basis of the strong magnetic field during MRI, the Hall effect means that a potential difference is produced when blood flows. The amplitude of the portion T of the ECG curve E which can be attributed to the Hall effect is therefore a measure of the flow of blood at the corresponding time. The amplitude in the portion A is therefore a measure of the flow of the blood from the heart during contraction, that is to say a measure of the cardiac output. The volume of blood expelled corresponds to the integral of the signal part which can be attributed to the Hall effect.

FIG. 3 schematically shows the measurement of the flow of blood F in an arbitrary blood vessel G in the patient P. The blood contains charge carriers Q. On the basis of the flow of blood in the direction F and on the basis of the magnetic field B (pointing to the side in FIG. 3), a potential difference $\Delta V$ is produced between two points P1, P2 in the vessel G. Positive charge carriers move to the top side of the vessel G in FIG. 3, and negative charge carriers move to the bottom side of the vessel G. Two electrodes 2 placed next to the vessel allow the potential V1, V2 at the points P1, P2 and hence the potential difference $\Delta V$ to be determined. The potential difference $\Delta V$ is proportional to the flow of blood.

FIG. 4 schematically shows at what points on the body electrodes are placed in order to record an ECG and in order to determine the cardiac output. To ascertain the cardiac output, at least two, typically three electrodes 2 in the arrangement shown in FIG. 4 are placed on the body of the patient P. This ascertains the flow of blood in the aorta, i.e. the cardiac output. Other devices, such as EEG, EOG or EMG, can be used in the same way.

Figure 5B:
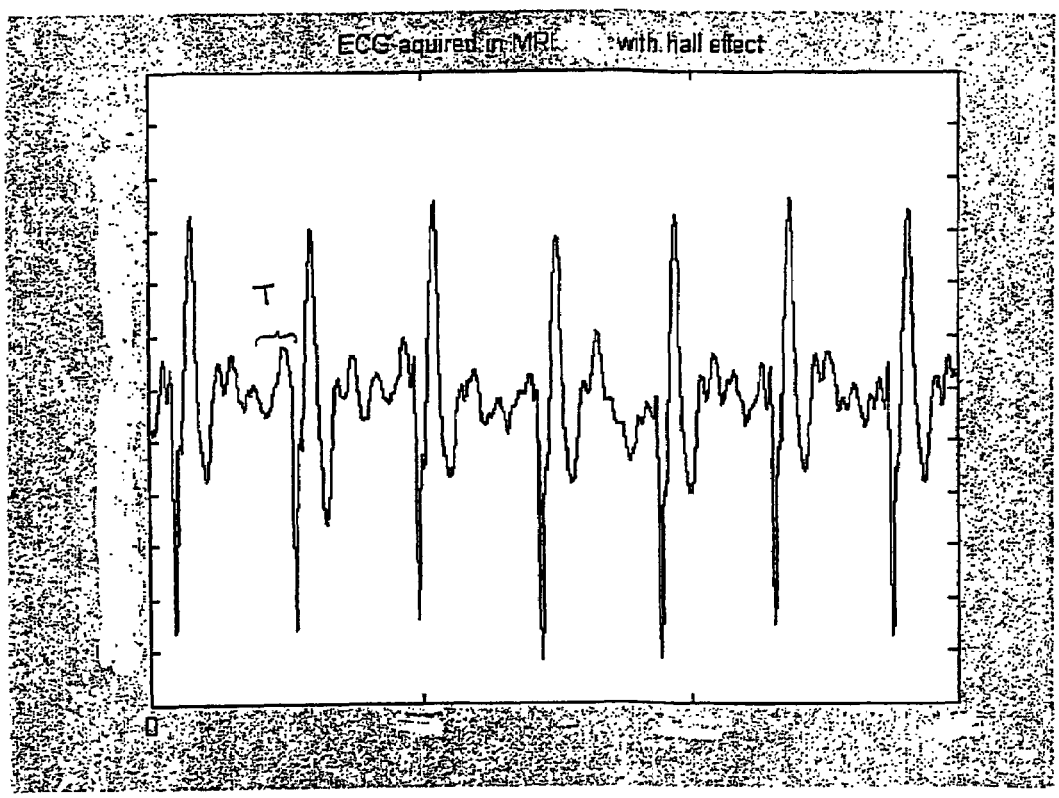

FIGS. 5a and 5b show the effect which a strong magnetic field has on the profile of an ECG signal on the basis of the Hall effect with the aid of an example.

FIG. 5a shows the ordinary profile of an ECG signal. In contrast to FIG. 5a, the signal shown in FIG. 5b has been recorded under the influence of a magnetic field within an MRI apparatus. The ECG signal has been overlaid with signal components T produced by the Hall effect. These signal components provide at least a qualitative, and when the cross-section of the corresponding blood vessel is known also a quantitative, measure of the flow of blood in the blood vessel, that is to say in the aorta in the case of an ECG, for example.

The invention claimed is:

1. A non-invasive method for acquiring and processing an electro-physiological ECG signal from a patient who is exposed to an extraneous magnetic field which produces interference in said ECG signal, said method comprising steps of:
   recording a signal by measuring potential differences between at least two points on a person's body surface near a blood vessel, the signal being an ECG signal overlaid with a magnetic interference component,
   determining a portion of said ECG signal curve in which the signal is overlaid with a signal component produced on the basis of the Hall effect on charge carriers in the blood flowing in the vessel, and subsequently
   processing the signal curve and eliminating the component of the signal which is brought about by the Hall effect in said portion of the signal curve.

2. A method according to claim 1, comprising a further step of determining the cardiac output on the basis of the determined signal curve profile in said portion of the signal curve.

3. An apparatus for acquiring and processing an electro-physiological signal, said apparatus comprising
   an ECG arrangement having at least two electrodes for measuring a potential difference between at least two points on a surface of the body near a blood vessel and for producing a potential signal, the signal being an electro-physiological ECG signal overlaid with interference signals due to the magnetic field, and
   means for ascertaining a component of the potential signal curve which is produced on the basis of the Hall effect by the movement of charge carriers in the vessel.

4. An apparatus according to claim 3, further comprising means for automatically determining the flow of blood on the basis of the determined component of the potential signal curve.

5. An apparatus according to claim 3, further comprising means for suppressing the component of the potential signal curve.

6. A non-invasive method for operating an electro-physiological instrument and for evaluating an electro-physiological signal acquired from a body exposed to a magnetic field by measuring potential differences between at least two points on a body surface near a blood vessel, the potential being overlaid with interference signals due to the magnetic field, said method comprising steps of determining a component of the signal curve which is caused by the Hall effect on charge carriers in blood flowing in the blood vessel and subsequently deriving from the component of the signal curve which is caused by the Hall effect a value which is characteristic of the flow of blood in a vessel.

* * * * *